United States Patent
Ikhlef

(10) Patent No.: US 8,917,812 B2
(45) Date of Patent: Dec. 23, 2014

(54) VARIABLE PITCH COLLIMATOR AND METHOD OF MAKING SAME

(75) Inventor: Abdelaziz Ikhlef, Hartland, WI (US)

(73) Assignee: General Electric Company, Schenectady, NY (US)

( * ) Notice: Subject to any disclaimer, the term of this patent is extended or adjusted under 35 U.S.C. 154(b) by 626 days.

(21) Appl. No.: 13/315,477

(22) Filed: Dec. 9, 2011

(65) Prior Publication Data

US 2013/0148777 A1     Jun. 13, 2013

(51) Int. Cl.
     *A61B 6/03*            (2006.01)

(52) U.S. Cl.
     USPC ............................................................ 378/19

(58) Field of Classification Search
     USPC ................. 378/4, 19, 98.8, 146–156
     See application file for complete search history.

(56) References Cited

U.S. PATENT DOCUMENTS

| | | | |
|---|---|---|---|
| 6,990,176 B2 * | 1/2006 | Sherman et al. | ............. 378/98.8 |
| 7,149,284 B2 | 12/2006 | Ikhlef | |
| 7,233,640 B2 | 6/2007 | Ikhlef et al. | |
| 7,399,119 B2 | 7/2008 | Chao et al. | |
| 7,455,454 B2 | 11/2008 | Ikhlef et al. | |
| 7,620,143 B2 | 11/2009 | Ikhlef et al. | |
| 7,869,559 B2 | 1/2011 | Ikhlef et al. | |
| 2003/0128801 A1 * | 7/2003 | Eisenberg et al. | ............. 378/19 |
| 2005/0082485 A1 * | 4/2005 | Torii | ......................... 250/361 R |

* cited by examiner

*Primary Examiner* — Iralki Kiknadze
(74) *Attorney, Agent, or Firm* — Ziolkowski Patent Solutions Group, SC

(57) ABSTRACT

An x-ray detector assembly includes a curved rail and a first plurality of x-ray attenuation plates attached to the curved rail, wherein the plates of the first plurality of x-ray attenuation plates are spaced apart from one another by a first pitch. A second plurality of x-ray attenuation plates are attached to the curved rail, wherein the plates of the second plurality of x-ray attenuation plates are spaced apart from the plates of the first plurality of x-ray attenuation plates by a second pitch greater than the first pitch. A first plurality of x-ray detector cells is also positioned adjacently to the first and second pluralities of x-ray attenuation plates and positioned in a linear arrangement with respect to each other.

20 Claims, 3 Drawing Sheets

VARIABLE PITCH COLLIMATOR AND METHOD OF MAKING SAME

BACKGROUND OF THE INVENTION

Embodiments of the invention relate generally to diagnostic imaging and, more particularly, to a collimator assembly having variable pitch collimator plates.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator assembly for collimating x-ray beams received at the detector, a scintillator for converting x-rays to light energy adjacent the collimator, and photodiodes for receiving the light energy from the adjacent scintillator and producing electrical signals therefrom.

Each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

The post patient x-ray collimator used in CT detection is a device mainly made of a highly absorbing material such as tungsten or molybdenum plates or high-Z material alloy aligned to a focal spot on the x-ray tube. The main function of the collimator is to select x-rays along a particular direction (primary beam from focal spot) and to reject scattered radiation from other directions (patient scattered radiation). For this purpose, collimating plates are placed in front of the scintillator pixels to eliminate scattered radiation from the patient. In one example, a collimator includes tungsten or molybdenum plates placed in front of the interfaces of the detector cells (detector septa), requiring high precision manufacturing and alignment/precision features within the individual parts for alignment purpose.

Typically, the pitch of the collimator plates is the same as the pitch of the scintillator pack (array) channels. However, because the pack is flat and does not follow a curved surface like the collimator, error may be accumulated from a misalignment point of view between the scintillator pack and the collimator. In this case, for a collimator having a collimator plate aligned with the septum between the center channels of a scintillator pack, the error will increase from the center of the scintillator pack toward the edge channels for each scintillator pack. The increasing error causes varying spectral performance and gain response as a function of focal spot motion of the scintillator pack channels.

Therefore, it would be desirable to design a collimator that improves the spectral performance and sensitivity of the scintillator pack channels.

BRIEF DESCRIPTION OF THE INVENTION

According to an aspect of the invention, an x-ray detector assembly includes a curved rail and a first plurality of x-ray attenuation plates attached to the curved rail, wherein the plates of the first plurality of x-ray attenuation plates are spaced apart from one another by a first pitch. A second plurality of x-ray attenuation plates are attached to the curved rail, wherein the plates of the second plurality of x-ray attenuation plates are spaced apart from the plates of the first plurality of x-ray attenuation plates by a second pitch greater than the first pitch. A first plurality of x-ray detector cells is also positioned adjacently to the first and second pluralities of x-ray attenuation plates and positioned in a linear arrangement with respect to each other.

According to another aspect of the invention, a CT system includes a rotatable gantry having an opening to receive an object to be scanned, an x-ray projection source positioned on the rotatable gantry and configured to project a beam of x-rays from a focal spot of the x-ray projection source toward the object, and a detector assembly positioned on the rotatable gantry. The detector assembly includes an array of detector cells configured to receive x-rays attenuated by the object, wherein the detector cells are separated from one another by a first distance. The detector assembly also includes a curved collimator rail and a collimator configured to collimate x-rays impinging thereon. The collimator includes a first plurality of plates positioned along the curved collimator rail and positioned adjacently to the array of detector cells, wherein the plates of the first plurality of plates are separated from one another by a first pitch. The collimator also includes a second plurality of plates positioned along the curved collimator rail and positioned adjacently to the array of detector cells, wherein the plates of the second plurality of plates are separated from the plates of the first plurality of plates by a second pitch greater than the first pitch.

According to yet another aspect of the invention, a method of making an x-ray detector assembly includes attaching a first plurality of x-ray attenuation plates to a rail having a curved profile, separating the plates of the first plurality of x-ray attenuation plates from one another by a first distance, and attaching a second plurality of x-ray attenuation plates to the rail. The method also includes separating the plates of the second plurality of x-ray attenuation plates from the plates of the first plurality of x-ray attenuation plates by a second distance greater than the first distance and positioning a planar pack of scintillator detector cells adjacently to the first and second pluralities of x-ray attenuation plates.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT)

system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
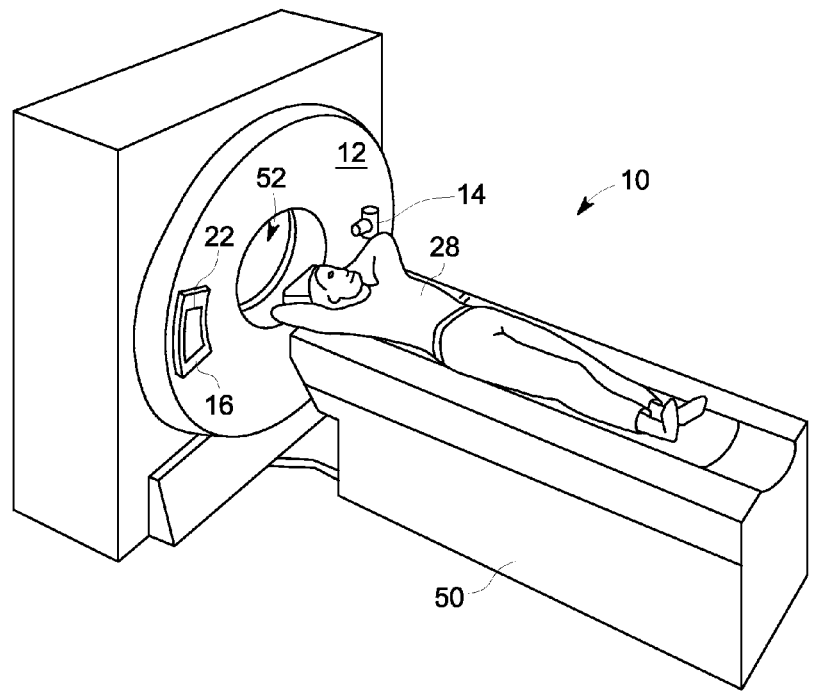
FIG. 1 is a pictorial view of a CT imaging system.
Figure 2:
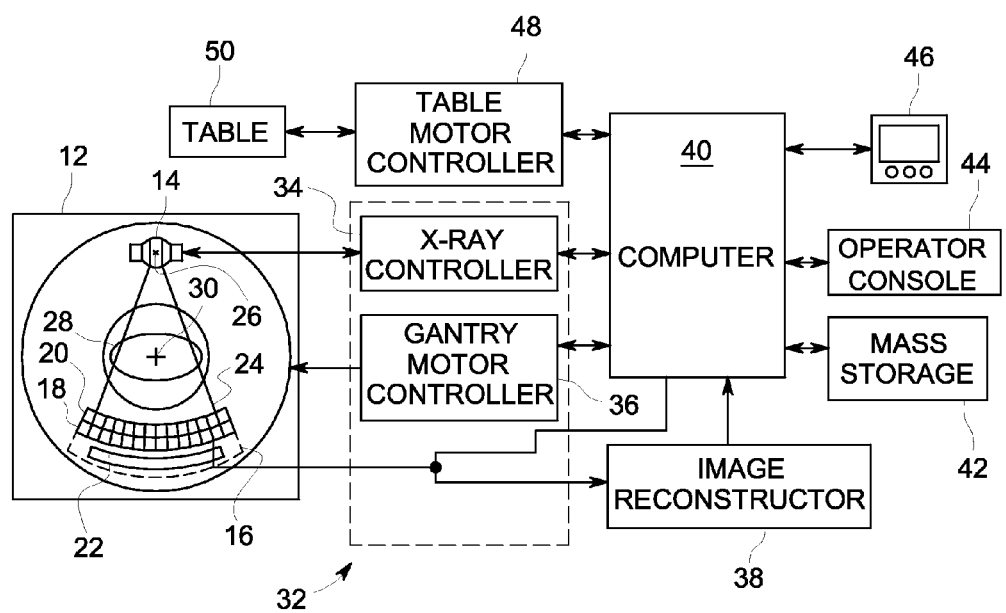
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly 16 on the opposite side of the gantry 12. Referring now to FIG. 2, detector assembly 16 is formed by a scintillator array 18, a collimator assembly 20, and a data acquisition system (DAS) 22. The detectors of scintillator array 18 sense the x-rays 24 projected from a focal spot 26 of x-ray source 14 that pass through a medical patient 28, and DAS 22 converts the data to digital signals for subsequent processing. Each scintillator array detector produces an analog electrical signal that represents the intensity of an impinging x-ray beam and hence the attenuated beam as it passes through the patient 28. During a scan to acquire x-ray projection data, gantry 12 and the components mounted thereon rotate about a center of rotation 30.

Rotation of gantry 12 and the operation of x-ray source 14 are governed by a control mechanism 32 of CT system 10. Control mechanism 32 includes an x-ray controller 34 that provides power and timing signals to an x-ray source 14 and a gantry motor controller 36 that controls the rotational speed and position of gantry 12. An image reconstructor 38 receives sampled and digitized x-ray data from DAS 22 and performs high speed reconstruction. The reconstructed image is applied as an input to a computer 40 which stores the image in a mass storage device 42.

Computer 40 also receives commands and scanning parameters from an operator via console 44 that has some form of operator interface, such as a keyboard, mouse, voice activated controller, or any other suitable input apparatus. An associated display 46 allows the operator to observe the reconstructed image and other data from computer 40. The operator supplied commands and parameters are used by computer 40 to provide control signals and information to DAS 22, x-ray controller 34 and gantry motor controller 36. In addition, computer 40 operates a table motor controller 48 which controls a motorized table 50 to position patient 28 and gantry 12. Particularly, table 50 moves patients 28 through a gantry opening 52 of FIG. 1 in whole or in part.

Figure 3:
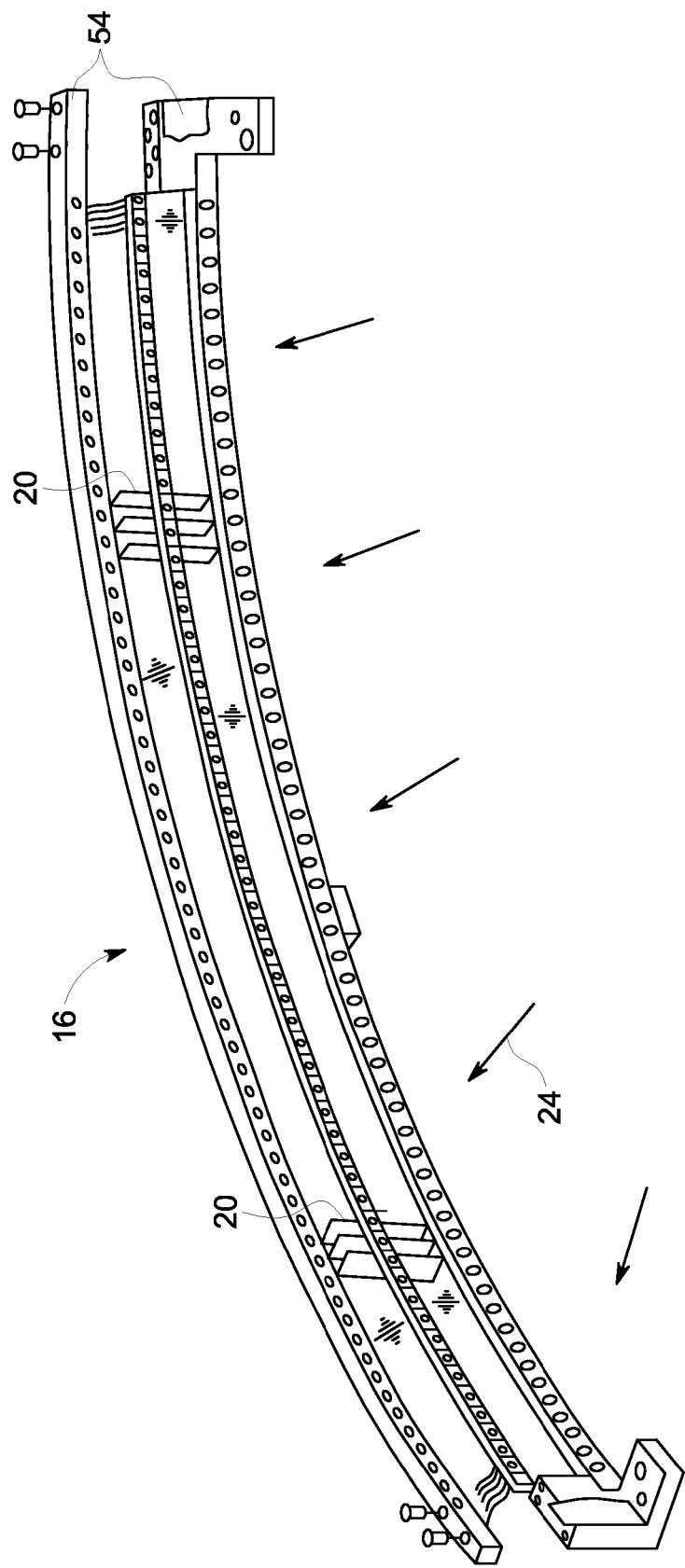
FIG. 3 is a perspective view of one embodiment of a CT system detector array.

As shown in FIG. 3, detector assembly 16 includes rails 54 along which plates of collimator assembly 20 may be placed. Collimator assembly 20 is positioned to collimate x-rays 24 before such beams impinge upon, for instance, scintillator array 18 of FIGS. 1 and 2.

Figure 4:
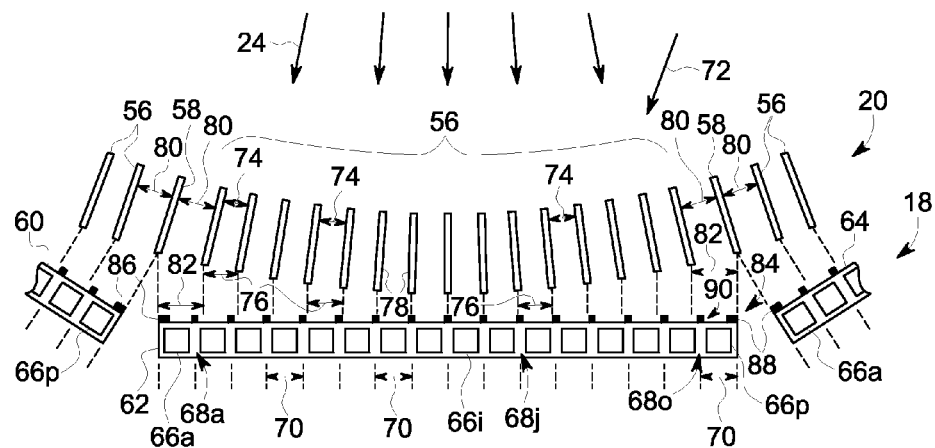
FIG. 4 is a schematic view of a detector assembly according to an embodiment of the invention.

FIG. 4 is a schematic view of detector assembly 16 of CT imaging system 10 shown in FIGS. 1 and 2 according to an embodiment of the invention. FIG. 3 shows collimator plates 56, 58 of collimator assembly 20 and scintillator packs 60, 62, 64 of scintillator array 18. Collimator plates 56, 58 are preferably constructed of tungsten, molybdenum, tantalum, a high z-material alloy, or other x-ray absorbing material. In one CT system embodiment, fifty-seven scintillator packs having sixteen channels each may be grouped together to form a 912-channel scintillator array. While only partially shown, it is contemplated that scintillator packs 60, 64 are constructed similarly to scintillator pack 62.

As shown in FIGS. 3 and 4, collimator assembly 20 is constructed such that collimator plates 56, 58 are aligned on curved collimator rail 54 such that the focus of the curvature and of the collimator plates 56, 58 is a common focal spot (such as focal spot 26 shown in FIG. 2) from which projected x-rays 24 emanate. While the profile of collimator assembly 20 is curved, the profile of each scintillator pack 60-64 is flat or planar such that the scintillators of each pack 60-64 are arranged in a linear pattern or arrangement within each pack 60-64. According to embodiments of the invention, collimator assembly 20 is constructed to minimize spectral non-linearity that can be caused by non-optimized placement of the collimator plates 56, 58 with respect to the collimator assembly 20.

As shown in FIG. 4, scintillator pack 60 includes sixteen scintillators 66*a*-66*p* with a grid of septa 68*a*-68*o* between each scintillator 66. It is to be understood that the scintillators 66*b*-66*o* between scintillators 66*a* and 66*p* and the septa 68*b*-68*n* between septa 68*a* and 68*o* are sequentially positioned and have not all been enumerated in FIG. 4 to simplify illustration of the reference numerals. The distance or pitch 70 between the centers of adjacent septa is constructed to be the same between all adjacent septa of scintillator pack 60. Accordingly, scintillators 66*a*-66*p* are positioned to be equally spaced apart from one another as well by pitch 70.

Collimator assembly 20 is positioned adjacently to scintillator pack 60-64 to collimate projected x-rays 24 and scattered x-rays 72 emitted toward collimator assembly 20. Collimator plates 56 are positioned to correspond with the septa 68 located between adjacent scintillators 66. Accordingly, fifteen collimator plates 56 correspond with the fifteen septa 68 located between neighboring or adjacent scintillators 66. Non-scattered x-rays 24 pass between adjacent collimator plates 56 and impinge on scintillators 66 while scattered x-rays 72 are rejected by collimator assembly 20.

While the fifteen collimator plates 56 correspond with the fifteen septa 68*a*-68*o* located between adjacent scintillators 66, the distance or pitch 74 between adjacent collimator plates 56 causes a separation 76 of adjacent collimator plates 56 to be less than the pitch 70 of septa 68. Pitch 74 may be an angular pitch related to the angular separation of adjacent collimator plates 56 with respect to a common point or a linear pitch measured in a common manner between collimator plates 56. According to an embodiment of the invention, pitch 74 is designed to be equal or equidistant throughout adjacent collimator plates 56. As shown in FIG. 4, the separation 76 between adjacent collimator plates 56 is measured between imaginary projection lines extending toward scintillator pack 62 from a common point along the bottom of each of the collimator plates 56 such as, for example, the center of the end 78 of each plate 56 closest to the scintillator pack 62, and the largest separation 76 is greater than pitch 70.

The collimator plates 56 corresponding with scintillator pack 62 are separated from the collimator plates 56 corresponding with scintillator packs 60 and 64 by a respective collimator plate 58. As such, each set of collimator plates 56 corresponding with a respective scintillator pack 60-64 is positioned between a pair of collimator plates 58. The distance or pitch 80 between a collimator plate 58 and an adjacent collimator plate 56 corresponding to any of scintillator packs 60-64 causes a separation 82 to be larger than pitch 70 or separation 76. Similar to separation 76, separation 82 may be measured between imaginary lines extending toward scintillator pack 62 from a bottom of a collimator plate 58 and the adjacent collimator plate 56. Accordingly, collimator assembly 20 is a variable pitch collimator. By varying pitches 74, 80 in this manner, scintillator packs 60-64 can be optimally positioned with respect to each other. Knowing that the spectral linearity may be caused by misalignment of plates the edges of the pixel, pitch 74 between plates 56 could be optimized in order to achieve optimal response sensitivity to different spectra by optimizing the coverage of the edges in the packs. Pitch 80, 90 will be bigger than 74 and the edge coverage will be achieved by adding a special grid 86, 88 at the edges of the pack.

Pitch 74 optimizes the spectral performance of scintillators 66 such that scintillators 66b-68o have a substantially similar spectral performance. That is, x-ray shadows (not shown) cast by collimator plates 56 as a result of blocking projected x-rays 24 have portions thereof that fall on septa 68 as well as on scintillators 66. These x-ray shadows equalize the active area of scintillators 66b-68o such that their spectral performance behaves substantially identically.

While the end-most collimator plates 56 corresponding with scintillator pack 62 respectively cast an x-ray shadow on the side of scintillators 66a and 66p corresponding with respective septa 68a and 68o, an x-ray absorbing grid 84 is positioned between scintillator pack 62 and collimator assembly 20 to ensure equalization of the spectral performance of scintillators 66a and 66p with scintillators 66b-68o. Grid 84 includes a first and a second portion or members 86, 88 positioned near a border of grid 84 and positioned adjacently to respective end scintillators 66a and 66p. Portions 86, 88 are sized and positioned to overlap scintillators 66a and 66p so as to create an x-ray shadow that, together with the x-ray shadow cast by the outermost collimator plates 56, equalizes the active area of scintillators 66a and 66p to that of scintillators 66b-68o such that the spectral performance of all scintillators 66 behaves substantially identically. In one embodiment, portions 86, 88 are constructed of tungsten, molybdenum, tantalum, a high z-material alloy, or other x-ray absorbing material.

A central portion 90 of grid 84 adds structural support for first and second portions 86 and 88, but the central portion 90 is designed lie within the x-ray shadows cast by collimator plates 56. As such, the central portion 90 of grid 84 need not be designed to completely block x-rays (through the edges of the pixels) as non-scattered x-rays 24 will instead be blocked by collimator plates 56. Central portion 90 may also be constructed of tungsten, molybdenum, tantalum, a high z-material alloy, or other x-ray absorbing material. Non-absorbing material could also be used in central portion 90 since these items are used for support and not for x-ray blockage.

Figure 5:
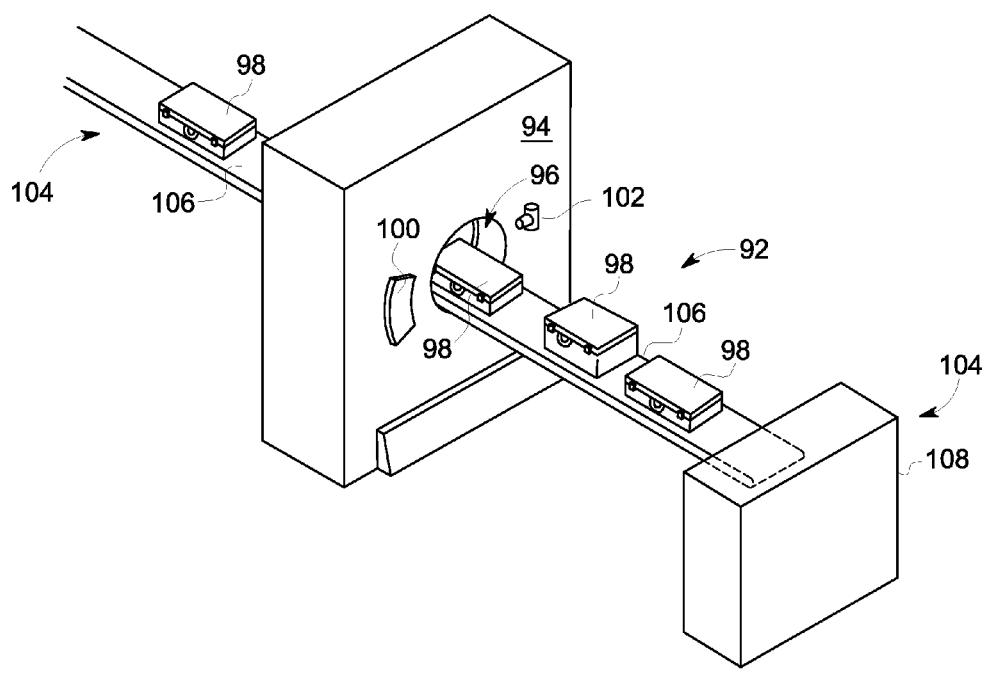
FIG. 5 is a pictorial view of a CT system for use with a non-invasive package inspection system.

Referring now to FIG. 5, is a pictorial view of an x-ray imaging system 92 for use with a non-invasive package inspection system. The x-ray system includes 92 a gantry 94 having an opening 96 therein through which a plurality of packages or pieces of baggage 98 may pass. The gantry 94 houses a detector assembly 100 such as one constructed according to embodiments of the invention described herein and a high frequency electromagnetic energy source, such as an x-ray tube 102. A conveyor system 104 is also provided and includes a conveyor belt 106 supported by a structure 108 to automatically and continuously pass packages or baggage pieces 98 through opening 96 to be scanned. Objects 98 are fed through opening 96 by conveyor belt 106, imaging data is then acquired, and the conveyor belt 106 removes the packages 98 from opening 96 in a controlled and continuous manner. As a result, postal inspectors, baggage handlers, and other security personnel may non-invasively inspect the contents of packages 98 for explosives, knives, guns, contraband, etc. One skilled in the art will recognize that gantry 94 may be stationary or rotatable. In the case of a rotatable gantry 94, system 92 may be configured to operate as a CT system for baggage scanning or other industrial or medical applications.

Therefore, according to an embodiment of the invention, an x-ray detector assembly includes a curved rail and a first plurality of x-ray attenuation plates attached to the curved rail, wherein the plates of the first plurality of x-ray attenuation plates are spaced apart from one another by a first pitch. A second plurality of x-ray attenuation plates are attached to the curved rail, wherein the plates of the second plurality of x-ray attenuation plates are spaced apart from the plates of the first plurality of x-ray attenuation plates by a second pitch greater than the first pitch. A first plurality of x-ray detector cells is also positioned adjacently to the first and second pluralities of x-ray attenuation plates and positioned in a linear arrangement with respect to each other.

According to another embodiment of the invention, a CT system includes a rotatable gantry having an opening to receive an object to be scanned, an x-ray projection source positioned on the rotatable gantry and configured to project a beam of x-rays from a focal spot of the x-ray projection source toward the object, and a detector assembly positioned on the rotatable gantry. The detector assembly includes an array of detector cells configured to receive x-rays attenuated by the object, wherein the detector cells are separated from one another by a first distance. The detector assembly also includes a curved collimator rail and a collimator configured to collimate x-rays impinging thereon. The collimator includes a first plurality of plates positioned along the curved collimator rail and positioned adjacently to the array of detector cells, wherein the plates of the first plurality of plates are separated from one another by a first pitch. The collimator also includes a second plurality of plates positioned along the curved collimator rail and positioned adjacently to the array of detector cells, wherein the plates of the second plurality of plates are separated from the plates of the first plurality of plates by a second pitch greater than the first pitch.

According to yet another embodiment of the invention, a method of making an x-ray detector assembly includes attaching a first plurality of x-ray attenuation plates to a rail having a curved profile, separating the plates of the first plurality of x-ray attenuation plates from one another by a first distance, and attaching a second plurality of x-ray attenuation plates to the rail. The method also includes separating the plates of the second plurality of x-ray attenuation plates from the plates of the first plurality of x-ray attenuation plates by a second distance greater than the first distance and positioning a planar pack of scintillator detector cells adjacently to the first and second pluralities of x-ray attenuation plates.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray detector assembly comprising:
a curved rail;
a first plurality of x-ray attenuation plates attached to the curved rail, wherein the plates of the first plurality of x-ray attenuation plates are spaced apart from one another by a first pitch;

a second plurality of x-ray attenuation plates attached to the curved rail, wherein the plates of the second plurality of x-ray attenuation plates are spaced apart from the plates of the first plurality of x-ray attenuation plates by a second pitch greater than the first pitch; and a first plurality of x-ray detector cells positioned adjacently to the first and second pluralities of x-ray attenuation plates and positioned in a linear arrangement with respect to each other.

2. The x-ray detector assembly of claim 1 wherein the first and second pluralities of x-ray attenuation plates are focused toward a common focal point.

3. The x-ray detector assembly of claim 2 wherein the first plurality of x-ray attenuation plates comprises:
a first subset of x-ray attenuation plates; and
a second subset of x-ray attenuation plates separated from the first subset of x-ray attenuation plates along in the curved rail by one x-ray attenuation plate of the second plurality of x-ray attenuation plates.

4. The x-ray detector assembly of claim 3 further comprising a second plurality of x-ray detector cells positioned adjacently to the second subset x-ray attenuation plates and positioned in a linear arrangement with respect to each other; and
wherein the first plurality of x-ray detector cells is positioned adjacently to the first subset of x-ray attenuation plates.

5. The x-ray detector assembly of claim 1 wherein the number of x-ray detector cells in the first plurality of x-ray detector cells is greater than the number of x-ray attenuation plates of the first plurality of x-ray attenuation plates.

6. The x-ray detector assembly of claim 1 wherein x-ray attenuation plates of the first plurality of x-ray attenuation plates are positioned to block x-rays emitted toward septa between the x-ray detector cells in the first plurality of x-ray detector cells.

7. The x-ray detector assembly of claim 6 wherein the septa are spaced apart from one another by a third pitch greater than the first pitch and less than the second pitch.

8. The x-ray detector assembly of claim 1 wherein x-ray attenuation plates of the first plurality of x-ray attenuation plates are positioned to equalize a spectral performance of the x-ray detector cells in the first plurality of x-ray detector cells.

9. The x-ray detector assembly of claim 8 further comprising a grid positioned between the first plurality of x-ray detector cells and the first plurality of x-ray attenuation plates and configured to attenuate x-rays impinging thereon, the grid comprising a pair of border members configured to attenuate x-rays from impinging on a pair of x-ray detector cells of the first plurality of x-ray detector cells.

10. The x-ray detector assembly of claim 9 wherein each cell of the pair of x-ray detector cells is positioned at a respective end of the first plurality of x-ray detector cells.

11. The x-ray detector assembly of claim 1 wherein the plates of the first and second pluralities of x-ray attenuation plates are configured to fully attenuate x-rays impinging thereon and are constructed of a material comprising one of tungsten, molybdenum, tantalum, and a high z-material alloy.

12. A CT system comprising:
a rotatable gantry having an opening to receive an object to be scanned;
an x-ray projection source positioned on the rotatable gantry and configured to project a beam of x-rays from a focal spot of the x-ray projection source toward the object;
a detector assembly positioned on the rotatable gantry and comprising:
an array of detector cells configured to receive x-rays attenuated by the object, wherein the detector cells are separated from one another by a first distance;
a curved collimator rail; and
a collimator configured to collimate x-rays impinging thereon and comprising:
a first plurality of plates positioned along the curved collimator rail and positioned adjacently to the array of detector cells, wherein the plates of the first plurality of plates are separated from one another by a first pitch;
a second plurality of plates positioned along the curved collimator rail and positioned adjacently to the array of detector cells, wherein the plates of the second plurality of plates are separated from the plates of the first plurality of plates by a second pitch greater than the first pitch.

13. The CT system of claim 12 wherein a space between neighboring detector cells of the array of detector cells forms a grid of septa; and
wherein the plates of the first plurality of plates are aligned toward a common focal point to prevent impingement of x-rays on the grid of septa and to prevent impingement of scattered x-rays on the detector cells.

14. The CT system of claim 13 wherein the first plurality of plates is positioned between the second plurality of plates.

15. The CT system of claim 13 wherein the array of detector cells is planar;
wherein each plate of the first plurality of plates has a bottom end positioned adjacently to the array of detector cells and is aligned with a respective septum of the grid of septa; and
wherein a distance between the bottom end of one of the plates of the first plurality of plates and the bottom end of an adjacent plate of the first plurality of plates is smaller than the first distance.

16. The CT system of claim 12 wherein the first and second pitches are angular pitches.

17. A method of making an x-ray detector assembly comprising:
attaching a first plurality of x-ray attenuation plates to a rail having a curved profile;
separating the plates of the first plurality of x-ray attenuation plates from one another by a first distance;
attaching a second plurality of x-ray attenuation plates to the rail;
separating the plates of the second plurality of x-ray attenuation plates from the plates of the first plurality of x-ray attenuation plates by a second distance greater than the first distance; and
positioning a planar pack of scintillator detector cells adjacently to the first and second pluralities of x-ray attenuation plates.

18. The method of claim 17 wherein positioning the planar pack of scintillator detector cells comprises aligning the plates of the first plurality of x-ray attenuation plates with a grid of septa formed among the cells of the planar pack of scintillator detector cells.

19. The method of claim 18 further comprising forming the planar pack of scintillator detector cells such that a distance between a center of one septum of the grid of septa and a center of an adjacent septum of the grid of septa is greater than the first distance.

20. The CT system of claim 17 further comprising positioning an x-ray attenuation grid between the first plurality of x-ray attenuation plates and the planar pack of scintillator detector cells.

* * * * *